United States Patent
Maywald et al.

(10) Patent No.: US 6,201,135 B1
(45) Date of Patent: Mar. 13, 2001

(54) METHOD FOR SEPARATING CONTAMINANTS FROM 3-(2'-ACETOXY-ETHYL-DIHYDRO-2(3H)-FURANONE

(75) Inventors: Volker Maywald, Ludwigshafen; Norbert Götz, Worms; Thomas Kükenhöhner, Böhl-Iggelheim; Dirk Borchers, Birkenheide; Hartmann König, Heidelberg; Horst Hartmann, Böhl-Iggelheim; Rupert Wagner, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/530,132
(22) PCT Filed: Dec. 2, 1998
(86) PCT No.: PCT/EP98/07832
  § 371 Date: Apr. 27, 2000
  § 102(e) Date: Apr. 27, 2000
(87) PCT Pub. No.: WO99/29680
  PCT Pub. Date: Jun. 17, 1999

(30) Foreign Application Priority Data

Dec. 8, 1997 (DE) .............................. 197 54 302

(51) Int. Cl.[7] .............................................. C07D 307/58
(52) U.S. Cl. .............................................. 549/323
(58) Field of Search ............................................ 549/323

(56) References Cited

U.S. PATENT DOCUMENTS

| | | | |
|---|---|---|---|
| 2,443,827 | * 6/1948 | Johnson | 549/322 |
| 4,831,166 | * 5/1989 | Eckhardt et al. | 549/323 |
| 4,837,346 | 6/1989 | Becker et al. | 549/425 |
| 5,283,326 | 2/1994 | Hansen et al. | 534/766 |
| 5,350,863 | * 9/1994 | Kuekenhoehner et al. | 549/323 |
| 5,371,246 | 12/1994 | Borchers et al. | 549/425 |
| 5,466,831 | * 11/1995 | Schnurr et al. | 549/323 |

FOREIGN PATENT DOCUMENTS

| | | |
|---|---|---|
| 246 581 | 11/1987 | (EP) . |
| 584 631 | 3/1994 | (EP) . |
| 588 224 | 3/1994 | (EP) . |

OTHER PUBLICATIONS

Packendorff et al. "Uber Einen Neuen Reaktions—Typus Des Athlyenoxyds (II). Uber Die Bei Der Kondensation Von Malonester Mit Athylenoxyd Entstehenden Nebenprodukte" Dokl. Akad. Nauk SSR 27 (1940) pp. 956–959.

* cited by examiner

*Primary Examiner*—Bernard Dentz
(74) *Attorney, Agent, or Firm*—Keil & Weinkauf

(57) ABSTRACT

A process for removing impurities from 3-(2'-acetoxyethyl)-dihydro-2(3H)-furanone (I), which comprises initially preparing the 3-(2'-acetoxyethyl)-dihydro-2(3H)-furanone containing the undesirable impurities in a manner known per se by acetylating 3-(2'-hydroxylethyl)-dihydro-2(3H)-furanone, subsequently treating it with strong mineral acids and finally removing the decomposition products of the undesirable impurities from I.

6 Claims, No Drawings

METHOD FOR SEPARATING CONTAMINANTS FROM 3-(2'-ACETOXY-ETHYL-DIHYDRO-2(3H)-FURANONE

The present invention relates to a process for removing undesirable impurities from 3-(2'-acetoxyethyl)dihydro-2 (3H)-furanone of the formula I

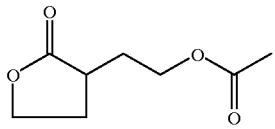

3-(2'-acetoxyethyl)dihydro-2(3H)-furanone is a starting material for preparing methyl tetrahydropyran-4-carboxylate, which for its part is an intermediate in the preparation of crop protection agents.

3-(2'-Acetoxyethyl)dihydro-2(3H)-furanone is prepared, for example, by processes that are known per se and described, for example, in U.S. Pat. No. 5,350,863, starting from methyl acetoacetate and ethylene oxide. Another process variant by which 3-(2r-acetoxyethyl)dihydro-2(3H)-furanone is obtainable is described in Dokl. Akad. Nauk SSSR 27 (1940), 956–959 and U.S. Pat. No. 5,283,326.

In both variants, the desired 3-(2'-acetoxyethyl)dihydro-2(3H)-furanone is formed as a mixture with a number of undesirable byproducts, in particular the isomeric dihydro-3-(2-methyl-1,3-dioxolan-2-yl)-2(3H)-furanone II

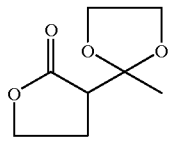

If I contaminated in this manner is reacted in a continuous gas phase reaction with methanol in the presence of acidic catalysts to give methyl tetrahydropyran-4-carboxylate, considerably lower yields and shorter catalyst onstream times are obtained than when a product of high purity without the byproducts is used. This is probably due to the fact that most byproducts contain sensitive acetal groups which decompose on the surface of the catalyst to oligomeric and polymeric products.

The removal by distillation in particular of II from mixtures comprising I and II can be realized only with difficulties and at high cost, owing to the boiling points, which are very close.

It is an object of the present invention to provide a process by which undesirable byproducts, in particular II, can be removed from mixtures with I without changing I in the process.

We have found that this object is achieved by a process for removing impurities from 3-(2'-acetoxyethyl)dihydro-2 (3H)-furanone (I), which comprises initially preparing the 3-(2'-acetoxyethyl)dihydro-2(3H)-furanone containing the undesirable impurities in a manner known per se by acetylating 3-(2'-hydroxyethyl)-dihydro-2-(3H)-furanone, subsequently treating it with strong mineral acids and finally removing the decomposition products of the undesirable impurities from I.

Surprisingly, the desired I is not degraded during treatment with mineral acids and can therefore be obtained in good yield and high purity.

Preferred embodiments of the process according to the invention are disclosed in the subclaims and the description below.

The process according to the invention starts with the mixture of 3-(2'-hydroxyethyl)dihydro-2(3H)-furanone and undesirable impurities which can be obtained by known processes which were described in the introduction.

This mixture is initially acetylated as completely as possible. Preferred acetylating agents are acetic anhydride or acetic acid itself; in principle, however, all acetylating agents known to the person skilled in the art for corresponding acetylations are suitable. The acetylation is generally carried out at temperatures in the range from 40° C. to 200° C., preferably from 60 to 140° C., over a period of from 0.5 to 10, preferably from 0.8 to 5 and in particular from 1 to 3, h.

To ensure complete acetylation, the acetylating agent is generally employed in a molar excess of from 5 to 50%, preferably from 5 to 20%, based on 3-(2'-hydroxyethyl) dihydro-2(3H)-furanone present in the mixture.

In the subsequent step, the acetylation product is treated with strong mineral acids. Preferred mineral acids are hydrochloric acid, nitric acid and, particularly preferably, sulfuric acid. This is employed preferably at at least 80% strength and in particular in the form of concentrated sulfuric acid.

The amount of sulfuric acid used can be varied within wide ranges; in some cases, it was found to be advantageous to use a molar ratio of strong mineral acid, based on the amount of acetylating agent used in the preceding step, in the range of from 1:20 to 1:3, preferably from 1:15 to 1:7 and in particular from 1:8 to 1:12.

For the treatment with the mineral acid, the temperature is generally in the range of from 10 to 80, preferably from 20 to 60 and in particular from 30 to 50° C. The duration of the treatment is generally in the range of from 0.3 to 10, in particular from 1 to 5, h, but can, in principle, be varied within wide limits.

After the treatment with strong mineral acids, the decomposition products of the undesirable impurities, in particular of dihydro-3-(2-methyl-1,3-dioxolan-2-yl)-2(3H)-furanone II, can be removed in a simple manner.

According to a preferred variant, the mineral acid is initially neutralized by addition of base, preferably aqueous alkali metal hydroxide, and the acetic acid formed as coproduct in the acetylation is subsequently, if appropriate, distilled off. Phase separation is subsequently carried out by addition of a suitable organic solvent and water, and the organic phase is then extracted. Suitable organic solvents are in particular aromatic hydrocarbons and especially alkylated benzene derivatives, such as xylene or toluene. The organic extracts are combined and the solvent is removed, and the residue can then be rectified under reduced pressure, giving, in good yield and high purity, the desired product, which may subsequently be processed further. The degree of purity of I can be increased even further by carrying out more than one rectifications in succession. The conditions for the rectification are known per se to the person skilled in the art and described in the literature, so that further details are not required here.

After the process according to the invention has been carried out, the purity of I is generally at least 98, preferably at least 98.5 and particularly preferably at least 99% by weight.

The I obtainable by the process according to the invention can be reacted in a manner known per se in high yield and with good catalyst onstream times to give methyl tetrahydropyran-4-carboxylate. This is an important intermediate in the preparation of crop protection agents.

EXAMPLE 1

Comparison

In a 3.5 l pressure vessel, a mixture of 1009 g (8.7 mol) of methyl acetoacetate, 1218 ml (969 g) of methanol and 110 g (0.61 mol) of a 30% strength solution of sodium methoxide in methanol was initially charged, and 765.6 g (17.4 mol) of ethylene oxide were subsequently pumped in at 60° C. with stirring over a period of 8 hours. The mixture was then stirred at 60° C. for 24 h. The reaction discharge was repeatedly flushed with nitrogen and subsequently transferred into a stirred apparatus having an attached column. The catalyst was then neutralized by addition of 29.6 g (0.3 mol) of sulfuric acid (96%). The low-boiling components, essentially methanol, methyl acetate and methyl glycol, were distilled off at 10 mbar (1013 Pa) up to a bottom temperature of 100° C. At 100° C., 806 g (7.9 mol) of acetic anhydride were added over a period of one hour with stirring to the distillation residue, and the mixture was then stirred at 100° C. for 2 h. The excess acetic anhydride and the acetic acid, which is formed as coproduct during the acetylation, were subsequently distilled off, and the crude discharge was cooled. After addition of 726 g of toluene and 300 g of water, the phases were separated and the aqueous phase was extracted twice with 200 ml of toluene each time. The organic extracts were combined and the solvent was stripped off under reduced pressure using a rotary evaporator. The residue was rectified batchwise under reduced pressure at 10 mbar (b.p. 161° C./10 mbar). This gave 1077 g (72%) of 3-(2'-acetoxyethyl)dihydro-2(3H)-furanone (calculated 100%).

Composition:

| | |
|---|---|
| 3-(2'-acetoxyethyl)dihydro-2(3H)-furanone | 95.0% |
| dihydro-3-(2-methyl-1,3-dioxolan-2-yl)-2(3H)-furanone | 3.5% |
| 3-(2'-hydroxyethyl)dihydro-2(3H)-furanon | 0.50% |
| others | 1.0% |

EXAMPLE 2

Single Batchwise Rectification

In a 3.5 l pressure vessel, a mixture of 1009 g (8.7 mol) of methyl acetoacetate, 1218 ml (969 g) of methanol and 110 g (0.61 mol) of a 30% strength solution of sodium methoxide in methanol was initially charged, and 765.6 g (17.4 mol) of ethylene oxide were subsequently pumped in at 60° C. with stirring over a period of 8 hours. The mixture was then stirred at 60° C. for 24 h. The reaction discharge was repeatedly flushed with nitrogen and subsequently transferred into a stirred apparatus having an attached column. The catalyst was then neutralized by addition of 29.6 g (0.3 mol) of sulfuric acid (96%). The low-boiling components, essentially methanol, methyl acetate and methyl glycol, were distilled off at 10 mbar up to a bottom temperature of 100° C. At 100° C., 806 g (7.9 mol) of acetic anhydride were added over a period of one hour to the distillation residue, and the mixture was then stirred at 100° C. for 2 h. To decompose the dihydro-3-(2-methyl-1,3-dioxolan-2-yl)-2(3H)-furanone, the reaction mixture was cooled to 40° C., 72.5 g (0.73 mol) of sulfuric acid (96%) were added and the mixture was then stirred at this temperature for 2 hours. To neutralize the sulfuric acid, 127.5 g (1.59 mol) of 50% strength NaOH were subsequently added at 40–45° C. The acetic acid which was formed as coproduct during the acetylation was distilled off and the crude discharge was cooled. After addition of 726 g of toluene and 850 g of water, the phases were separated and the aqueous phase was extracted twice with 200 ml of toluene each time. The organic extracts were combined and the solvent was stripped off under reduced pressure using a rotary evaporator. The residue was rectified batchwise under reduced pressure at 10 mbar (b.p. 161° C./10 mbar). This gave 1056 g (71%) of 3-(2'-acetoxyethyl)dihydro-2(3H)-furanone (calculated 100%).

Composition:

| | |
|---|---|
| 3-(2'-acetoxyethyl)dihydro-2(3H)-furanone | 98.5% |
| dihydro-3-(2-methyl-1,3-dioxolan-2-yl)-2(3H)-furanone | 0.3% |
| 3-(2'-hydroxyethyl)dihydro-2(3H)-furanon | 0.3% |
| others | 0.9% |

EXAMPLE 3

Three-Fold Continuous Rectification

In a 1 m$^3$ pressure vessel, a mixture of 348 kg (3.0 kmol) of methyl acetoacetate, 420.1 l (334.2 kg) of methanol and 37.9 kg (210.3 mol) of a 30% strength solution of sodium methoxide in methanol was initially charged and 264.1 kg (6.0 kmol) of ethylene oxide were subsequently pumped in with stirring at 60° C. over a period of 8 hours. The mixture was then stirred at 60° C. for 24 h. The reaction discharge was repeatedly flushed with nitrogen and subsequently transferred into a 1 m3 [sic] stirred apparatus having an attached column. The catalyst was then neutralized by addition of 10.2 kg (103.5 mol) of sulfuric acid (96%). The low-boiling components, essentially methanol, methyl acetate and methyl glycol, were distilled off at 10 mbar (1013 Pa) up to a bottom temperature of 100° C. At 100° C., 278 kg (2.7 kmol) of acetic anhydride were added with stirring over a period of one hour to the distillation residue, and the mixture was then stirred at 100° C. for 2 h. To decompose the dihydro-3-(2-methyl-1,3-dioxolan-2-yl)-2(3H)-furanone, the reaction mixture was cooled to 40° C., 25.0 kg (251.8 mol) of sulfuric acid (96%) were added and the mixture was then stirred at this temperature for two hours. To neutralize the sulfuric acid, 439.7 kg (548 mol) of 50% strength NaOH were subsequently added at 40–45° C. The acetic acid formed as coproduct during the acetylation was distilled off and the crude discharge was cooled. After addition of 250.4 kg of toluene and 293.2 kg of water, the phases were separated and the aqueous phase was extracted twice with 100 kg of toluene each time. The organic extracts were combined and processed further. This gave 375.3 kg (73%) of 3-(2'-acetoxyethyl)dihydro-2(3H)-furanone (calculated 100%).

Composition:

| | |
|---|---|
| 3-(2'-acetoxyethyl)dihydro-2(3H)-furanone | 99.5% |
| dihydro-3-(2-methyl-1,3-dioxolan-2-yl)-2(3H)-furanone | <0.1% |
| 3-(2'-hydroxyethyl)dihydro-2(3H)-furanon | 0.3% |
| others | 0.1% |

To investigate the effects of the degree of purity of I on the subsequent reaction, the products obtained by Examples 1 to 3 were converted into methyl tetrahydropyran-4-carboxylate according to the following general equation:

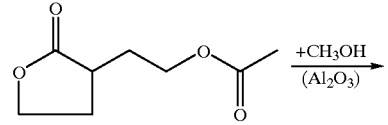

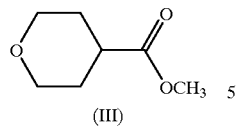

(III)

Per hour, a solution consisting of 172 g of 3-(2'-acetoxyethyl)dihydro-2(3H)-furanone and 192 g of methanol was evaporated and passed in a tubular reactor at 250° C. over 2000 g of a γ-aluminum oxide catalyst (Pural SB™, formed into 2 mm strands, dried for 16 h at 120° C. and calcined for 3 h at 520° C.). The gaseous reaction discharge was condensed and the resulting tetrahydropyran-4-carboxylate ester was purified by batchwise distillation (b.p. 117° C./30 mbar).

The results of the reactions of 3-(2'-acetoxyethyl)dihydro-2(3H)-furanone I with different proportions of dihydro-3-(2-methyl-1,3-dioxolan-2-yl)-2(3H)-furanone II are summarized in Table 1:

TABLE 1

| Proportion of II in % | Conversion (%) | Yield of III, at the start | Yield of III, after 60 h | Yield of III, after 1200 h | Yield of III, after 1440 h |
|---|---|---|---|---|---|
| 3.5 (Ex.1) | 100 | 55% | 39% | — | — |
| 0.3 (Ex.2) | 100 | 68% | 68% | 68% | 57% |
| <0.1 (Ex.3) | 100 | 68% | 68% | 68% | 68% |

The results of the table above show the strong effect of the content of impurities, in particular II, on the further processing of I.

We claim:

1. A process for removing impurities from 3-(2'-acetoxyethyl)-dihydro-2(3H)-furanone (I), which comprises initially preparing the 3-(2'-acetoxyethyl)dihydro-2(3H)-furanone containing the undesirable impurities in a manner known per se by acetylating 3-(2'-hydroxyethyl)-dihydro-2-(3H)-furanone, subsequently treating it with strong mineral acids and finally removing the decomposition products of the undesirable impurities from I.

2. A process as defined in claim 1, wherein the acetylating agent used is acetic anhydride or acetic acid.

3. A process as defined in claim 1, wherein the strong mineral acid used is sulfuric acid.

4. A process as defined in claim 1, wherein the treatment with sulfuric acid is carried out at temperatures of from 20 to 70° C.

5. A process as defined in claim 1, wherein the decomposition products are removed by phase separation, subsequent extraction and distillation or rectification.

6. A process as defined in claim 5, wherein a multi-step distillation or rectification is carried out.

* * * * *